(12) United States Patent
Edic et al.

(10) Patent No.: US 10,898,159 B2
(45) Date of Patent: Jan. 26, 2021

(54) X-RAY IMAGING SYSTEM USE AND CALIBRATION

(71) Applicant: General Electric Company, Schenectady, NY (US)

(72) Inventors: Peter Michael Edic, Albany, NY (US); Biju Jacob, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 16/245,938

(22) Filed: Jan. 11, 2019

(65) Prior Publication Data

US 2020/0222024 A1 Jul. 16, 2020

(51) Int. Cl.
*A61B 6/00* (2006.01)
*G01N 23/046* (2018.01)
*A61B 6/03* (2006.01)

(52) U.S. Cl.
CPC .............. *A61B 6/587* (2013.01); *A61B 6/032* (2013.01); *A61B 6/582* (2013.01); *G01N 23/046* (2013.01); *G01N 2223/303* (2013.01)

(58) Field of Classification Search
CPC ......... A61B 6/587; A61B 6/032; A61B 6/582; G01N 23/046; G01N 2223/303
USPC ........................................................ 378/205
See application file for complete search history.

(56) References Cited

U.S. PATENT DOCUMENTS

| | | | |
|---|---|---|---|
| 5,079,426 A | 1/1992 | Antonuk et al. | |
| 5,430,785 A | 7/1995 | Pfoh et al. | |
| 5,550,886 A * | 8/1996 | Dobbs | A61B 6/032 378/19 |
| 5,608,776 A * | 3/1997 | Hsieh | G21K 1/04 378/145 |
| 5,657,364 A * | 8/1997 | Pfoh | A61B 6/035 378/137 |
| 5,706,326 A | 1/1998 | Gard | |
| 6,370,218 B1 * | 4/2002 | Toth | A61B 6/032 378/113 |
| 6,385,279 B1 * | 5/2002 | Toth | A61B 6/032 378/11 |
| 7,266,179 B2 * | 9/2007 | Deuringer | H01J 35/14 378/137 |
| 8,761,483 B2 | 6/2014 | Suzuki et al. | |

(Continued)

OTHER PUBLICATIONS

Hein, Ilmar A., et al.; "Lateral (xy) Direction Balanced Flying Focal Spot Helical Cone-Beam CT Algorithm", IEEE Nuclear Science Symposium Conference Record, 2007, pp. 2624-2629.

(Continued)

*Primary Examiner* — Taeho Jo
(74) *Attorney, Agent, or Firm* — Fletcher Yoder, P.C.

(57) ABSTRACT

The present disclosure relates to determining the position of an X-ray focal spot in real time during an imaging process and using the focal spot position to ensure alignment of the focal spot and high-aspect detector elements or to correct for focal spot misalignment, thereby mitigating image artifacts. For example, the focal spot position may be monitored and may be adjusted in real-time using electromagnetic electron beam steering during a scan. Alternatively, previously determined functional relationships between focal spot position and measured data may be applied to address or correct for focal spot misalignment in the acquired data.

22 Claims, 7 Drawing Sheets

(56) References Cited

U.S. PATENT DOCUMENTS

| | | | |
|---|---|---|---|
| 2006/0182228 A1* | 8/2006 | Toth | A61B 6/032 378/205 |
| 2006/0251210 A1* | 11/2006 | Chao | A61B 6/585 378/19 |
| 2009/0060140 A1* | 3/2009 | Subraya | H01J 35/14 378/125 |
| 2010/0002829 A1* | 1/2010 | Dafni | A61B 6/4028 378/9 |
| 2010/0204942 A1 | 8/2010 | Danielsson et al. | |
| 2011/0176663 A1* | 7/2011 | Shaughnessy | A61B 6/08 378/154 |
| 2012/0012742 A1* | 1/2012 | Ren | A61B 6/035 250/252.1 |
| 2012/0177272 A1* | 7/2012 | Suzuki | A61B 6/587 382/131 |
| 2012/0236987 A1* | 9/2012 | Ruimi | A61B 6/4028 378/19 |
| 2012/0328076 A1* | 12/2012 | Ikhlef | G21K 1/025 378/62 |
| 2013/0121475 A1* | 5/2013 | Deych | G21K 1/00 378/154 |
| 2013/0121478 A1* | 5/2013 | Hansroul | G01T 7/005 378/207 |
| 2014/0042333 A1* | 2/2014 | Niederlohner | A61B 6/4233 250/394 |
| 2014/0140469 A1* | 5/2014 | Carmi | A61B 6/4233 378/9 |
| 2014/0205073 A1* | 7/2014 | Tkaczyk | H01J 35/26 378/126 |
| 2016/0113603 A1* | 4/2016 | Schirra | A61B 6/032 250/252.1 |
| 2016/0199019 A1* | 7/2016 | Ruimi | A61B 6/5258 378/9 |
| 2017/0318651 A1* | 11/2017 | Canfield | H01J 35/14 |
| 2017/0318652 A1* | 11/2017 | Meiler | A61B 6/582 |
| 2018/0177481 A1* | 6/2018 | Jacob | G01N 23/046 |
| 2018/0296117 A1* | 10/2018 | Sra | A61B 6/5288 |
| 2018/0317869 A1* | 11/2018 | Rui | A61B 6/06 |
| 2018/0328863 A1* | 11/2018 | Rui | A61B 6/5282 |
| 2019/0008474 A1* | 1/2019 | Sjolin | A61B 6/4291 |

OTHER PUBLICATIONS

Vogeler, Frederik, et al.; "Positional Stability of 2D X-Ray Images for Computer Technology", International Symposium on Digital Industrial Radiology and Computed Comography—Mo.3.3, 2011, 9 pages.

De Oliveira, Fabricio Borges, et al.; "Characterization and Correction of Geometric Errors Induced by Thermal Drift in CT Measurements", 2014, vol. 613, pp. 327-334.

* cited by examiner

X-RAY IMAGING SYSTEM USE AND CALIBRATION

TECHNICAL FIELD

Embodiments of the present specification relate generally to maintaining focal spot alignment in certain imaging contexts and/or acquisition and use of calibration data after an imaging scan has been completed.

BACKGROUND

In an imaging system, such as a computed tomography (CT) imaging system, a fan- or cone-shaped X-ray beam is emitted towards an object such as a patient, a piece of luggage, or other object to image a region of interest in the object. The beam is typically attenuated by the object. Subsequently, the attenuated beam is incident on a CT detector having an array of detector elements. In response to the attenuated beam, the detector elements of the array generate respective electrical signals representative of internal structure or information of the object. These electrical signals are processed by a data processing unit to generate an image representative of the region of interest in the object.

In certain X-ray detection techniques, direct-conversion sensors comprising low atomic number materials, such as silicon, may be employed. Due to the limited X-ray absorption of these materials, the detector elements used in such sensing techniques may have significant depth (e.g., greater than 25 mm, such as 35 mm to 40 mm) relative to other X-ray sensing elements that employ high atomic number direct-conversion sensor material (e.g., composed of cadmium/zinc/telluride or cadmium/telluride) or a conversion material intermediary layer, such as a scintillator, which may be 2 mm to 3 mm thick. For each type of conversion material, the depth is chosen to achieve high detection efficiency, i.e., to attenuate mostly all (>90%) of photons incident upon the detector. In the description that follows, we use silicon as a representative of one embodiment of a low atomic number, direct-conversion X-ray sensor; however, any suitable sensor material with the appropriate attenuation properties is envisioned. X-ray incidence may be measured at different depths along the length of the silicon elements in such direct-conversion detectors such that the silicon elements may be considered to have different depth segments that correspond to different X-ray spectral energy when measured.

Due to their relative length in one dimension (e.g., the Y dimension) and the desire for high resolution (corresponding to millimeter or sub-millimeter resolution) in a plane perpendicular (e.g., an X-Z plane) to this long dimension, the silicon detector elements may have a very high aspect ratio (i.e., the ratio of depth to the width and/or length of the detector elements). This geometry in combination with the highly-attenuating foils that may be present between respective silicon wafers forming the detector elements (e.g., used to mitigate intra-detector Compton scattering) may lead to X-rays being blocked or attenuated if the focal spot from which X-rays are emitted shifts during operation, which may occur as the anode in the X-ray tube is heated. When the system is in alignment, these photons would otherwise interact with the detector. This loss of data can be associated with image artifacts which may be detrimental in the image reconstruction context.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one implementation, a method is provided for generating calibration data. In accordance with this method, X-rays are emitted from a focal spot of an X-ray source at a plurality of positions in one or more spatial dimensions. For each position, paired response data is generated. The paired response data comprises a first measurement from a first detector element of a sensor pair and a second measurement from a second detector element of the sensor pair. The first detector element and the second detector element of the sensor pair have complementary response functions with respect to movement of the focal spot in the one or more dimensions. At least the paired response data and corresponding positions in the one or more spatial dimensions are associated to generate one or more functional relationships.

In a further implementation, a method is provided for addressing X-ray focal spot misalignment. In accordance with this method, X-rays are emitted from an X-ray source comprising a focal spot. The X-rays pass through an imaging volume in which a patient or object being scanned is positioned. Response data is acquired from one or more reference sensor pairs positioned where the X-rays incident on the reference sensor pairs do not pass through the patient or object. The response data for each reference sensor pair comprises a first measurement from a first detector element of the respective sensor pair and a second measurement from a second detector element of the respective sensor or pair. The first detector element and the second detector element of the each reference sensor pair have complementary response functions with respect to movement of the focal spot in one or more spatial dimensions. A position in the one or more spatial dimensions of the focal spot is determined using the response data from the one or more reference sensor pairs. Corrective action is performed based on the position of the focal spot in the one or more spatial dimensions.

In an additional implementation, an X-ray imaging system is provided. In accordance with this implementation, the X-ray imaging system comprises: an X-ray source configured to emit X-rays from a focal spot during operation and a detector configured to generate signals corresponding to X-ray intensity when exposed to X-ray emission by the X-ray source. The detector comprises a plurality of sensor pairs, each sensor pair comprising a first detector element and a second detector element separated by an attenuating layer and having complementary response functions with respect to position of the focal spot in one or more spatial dimensions. The X-ray imaging system further comprises one or more processing circuits configured to: cause emission of X-rays from the X-ray source, wherein the X-rays pass through an imaging volume in which a patient or object being scanned is positioned during operation; acquire response data from one or more reference sensor pairs of the plurality of sensor pairs, wherein the reference sensor pairs are positioned where the X-rays incident on the reference sensor pairs do not pass through the patient or object; determine a position of the focal spot in the one or more spatial dimensions using the response data from the one or more reference sensor pairs; and perform corrective action based on the position of the focal spot in the one or more spatial dimensions.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Figure 1:
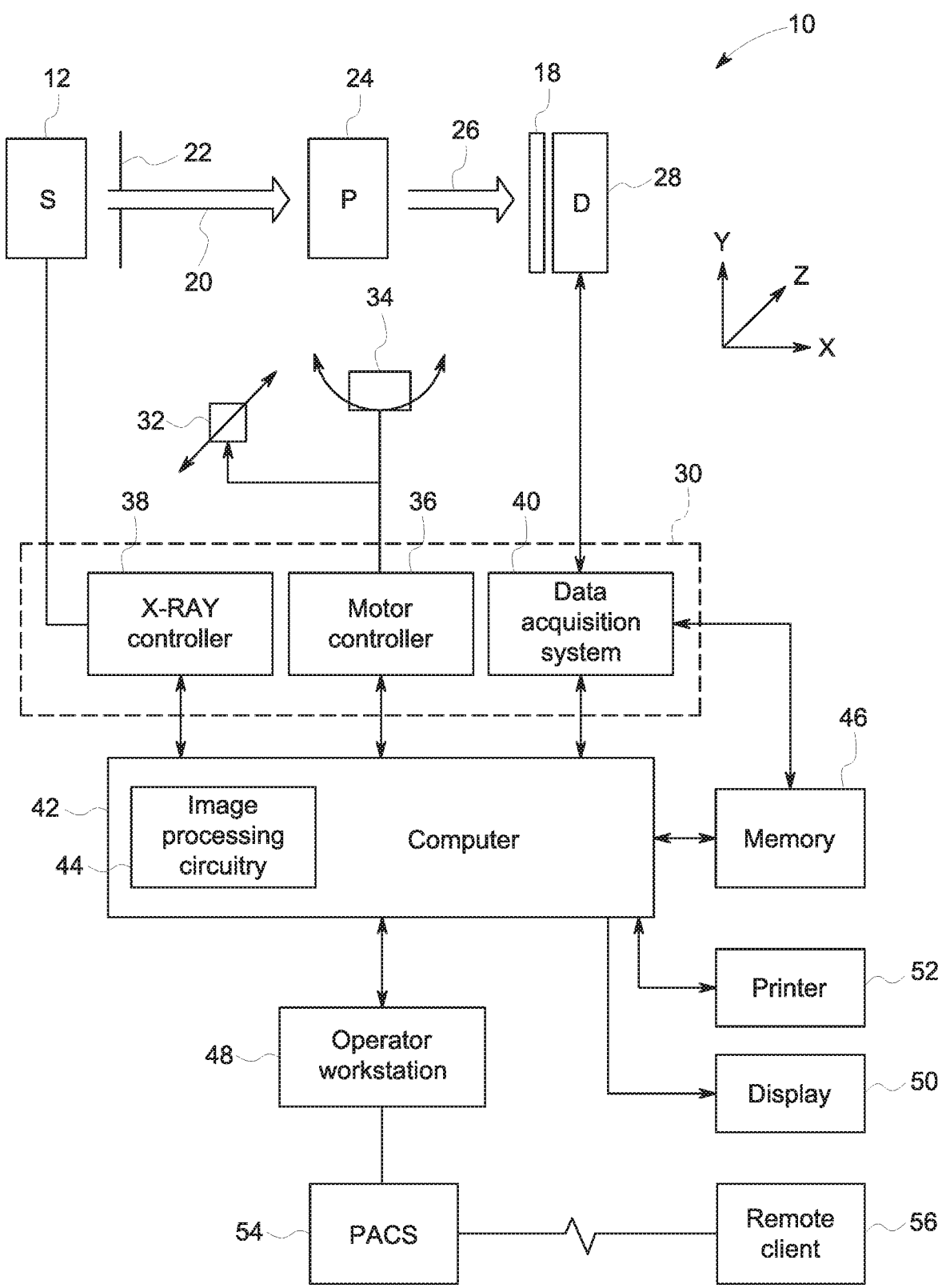
FIG. 1 is a block diagram representation of a CT system, in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic imaging for industrial CT used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context or image processing field where X-ray transmission data is acquired using high-aspect ratio detector elements.

The present technique relates to the use of direct-conversion sensors in X-ray detectors, such as may be used in either single-energy or multi-energy CT. During at CT acquisition, the focal spot in the X-ray tube may be in a different position relative to when calibration data were acquired due to recently-executed CT scans or may move during an extended scan due to heating of the anode. The misalignment or motion of the focal spot may lead to image artifacts. One technique to mitigate focal spot motion during a scan is to use alternate detector elements with reduced depth (higher X-ray attenuation capability) to reduce the consequences of focal spot misalignment events. For energy-discriminating, photon-counting detectors that may be used in CT, the direct-conversion materials often employed are cadmium-telluride (CdTe) or cadmium-zinc-telluride (CZT). However, there are many known issues with these sensor materials including, but not limited to, charge sharing, k-edge fluorescence, charge trapping, reduced count rate capability, and material response instability and nonuniformity. These issues may reduce the desirability of using these direct-conversion materials. As discussed herein, silicon may instead be employed as a direct-conversion material due to its desirable properties that mitigate one or more of the issues identified above. However, the use of silicon as a sensor material presents other challenges, such as the limited X-ray absorption provided by this direct-conversion sensor material.

With this in mind, techniques are described herein to facilitate the use of silicon as a direct conversion material for use in X-ray detectors. However, it should be understood that, despite the present examples and discussion being generally directed to silicon embodiments, other suitable low atomic number, direct-conversion materials may benefit from the presently disclosed techniques and are intended to be encompassed by the present discussion. As noted above, due to limited X-ray absorption provided by silicon, silicon-based detector elements (i.e., pixels) used in such direct-conversion X-ray sensing may have significant depth (e.g., 35 mm to 40 mm) and in energy-resolving and/or photon-counting implementations may be segmented such that signals can be acquired at different depths along the detector element. Moreover, discrete silicon wafers may be used to fabricate rows of the detector, with attenuating foil or material provided between wafers to mitigate scattered photons in the detector. Alternatively, alternating wafers and attenuating foil may be positioned to fabricate columns of the detector. Therefore, with the preceding in mind, the silicon detector elements have a very high aspect ratio (i.e., the ratio of the detector depth to its width and/or length).

Each silicon wafer is focally-aligned to the X-ray focal spot from which X-ray emission occurs. As the anode of the X-ray source heats from previous scans and/or during operation, both the lateral and longitudinal focal spot positions may change. Additionally, gantry rotation during a CT scan may cause changes in the focal spot position. Due to the high aspect ratio of the silicon detector elements and the highly-attenuating foils that are placed between individual silicon wafers, any misalignment of detector elements with the focal spot can impact the incidence of X-rays at different depths of the misaligned detector element. In accordance with the present technique, such focal-spot misalignment can be discerned from analysis of one or more reference detectors or other suitable detector measurements (e.g., other detector elements or special source-side reference detectors). By way of example, a gain sensitivity function in conjunction with such reference signals may be used to detect misalignment and enable corrective measures to be taken.

In further aspects of the present technique, the position of the X-ray focal spot may be estimated and modified in real time during CT scanning to ensure focal alignment of the focal spot and high-aspect-ratio detector elements, thereby mitigating image artifacts. For example, the focal spot position may be monitored and adjusted in real-time using electromagnetic electron beam steering during a CT scan. Such real-time focal spot position adjustment may be useful: (1) to address or otherwise compensate for focal spot motion (one or more of axially and transaxially) during scanning, (b) to mitigate image artifacts resulting from the motion of the focal spot during scanning, and/or (c) to simplify system calibration techniques.

In another aspect, calibration data may be acquired to allow calibration and/or correction of CT projection data after a scan has been completed. For example, in lieu of real-time focal spot adjustment, electromagnetic electron beam steering may be leveraged to modify the position (one or more of axially and transaxially) of the focal spot to acquire requisite calibration data. The focal spot position may be monitored and/or estimated during a scan using measurement data acquired from reference detectors or other suitable detectors (e.g., other detector elements or special source-side reference detectors). Acquired projection data may then be corrected using the calibration data and using estimates of the focal spot position data acquired at one or more angular positions of the object with respect to the CT gantry.

With the preceding discussion in mind, FIG. 1 illustrates an embodiment of an imaging system 10 for acquiring and processing image data using vertically-segmented detector elements in accordance with structures and approaches discussed herein. In the illustrated embodiment, system 10 is a CT system designed to acquire X-ray projection data and to reconstruct the projection data into volumetric reconstructions for display and analysis. The CT imaging system 10 includes one or more X-ray sources 12, such as one or more X-ray tubes or solid-state emission structures which allow X-ray generation at one or more locations and/or one or more energy spectra during an imaging session.

In certain implementations, the X-ray source 12 may be positioned proximate to a pre-patient collimator/filter assembly 22 that may be used to steer the X-ray beam 20, to define the shape (such as by limiting off-angle emissions) and/or extent of a high-intensity region of the X-ray beam 20, to control or define the energy profile of the X-ray beam 20, and/or to otherwise limit X-ray exposure on those portions of the patient 24 not within a region of interest. In practice, the filter assembly or beam shaper 22 may be incorporated within the gantry, between the source 12 and the imaged volume.

The X-ray beam 20 passes into a region in which the subject (e.g., a patient 24) or object of interest (e.g., manufactured component, baggage, package, and so forth) is positioned. The subject attenuates at least a portion of the X-ray photons 20, resulting in attenuated X-ray photons 26 that impinge upon a pixelated detector array 28 formed by a plurality of detector elements (e.g., pixels) arranged in an m×n array. The detector elements may comprise one or more segments along the length of X-ray travel in the detector. The detector 28 may be an energy-integrating detector, a photon-counting detector, an energy-discriminating detector, or any other suitable radiation detector. By way of example, the detector 28 may be an energy-discriminating photon-counting detector, whose output signals, generated in response to X-rays incident on the detector, convey information about the number and energy of photons that impinge upon the detector at measured positions and over a time interval corresponding to a scan or imaging session. For example, the output signals of the elements of the detector 28 may constitute photon counts for each of a plurality of energy bins (i.e., energy ranges) for a given acquisition interval. The electrical signals are acquired and processed to generate one or more projection datasets. In the depicted example, the detector 28 is coupled to the system controller 30, which commands acquisition of the digital signals generated by the detector 28.

A system controller 30 commands operation of the imaging system 10 to execute filtration, examination and/or calibration protocols, and may process the acquired data. With respect to the X-ray source 12, the system controller 30 furnishes power, focal spot location, control signals and so forth, for the X-ray examination sequences. In accordance with certain embodiments, the system controller 30 may control operation of the pre-patient collimator/filter assembly 22, the CT gantry (or other structural support to which the X-ray source 12 and detector 28 are attached), and/or the translation and/or inclination of the patient support over the course of an examination.

In addition, the system controller 30, via a motor controller 36, may control operation of a linear positioning subsystem 32 and/or a rotational subsystem 34 used to move the subject 24 and/or components of the imaging system 10, respectively. For example, in a CT system, the radiation source 12 and detector 28 rotate about the object (e.g., patient 24) to acquire X-ray transmission data over a range of angular positions or views. Thus, in a real-world implementation, the imaging system 10 is configured to generate X-ray transmission data corresponding to each of the plurality of angular positions (e.g., 360°, 180°+a fan beam angle (α), and so forth) covering an entire scanning area of interest. In alternate embodiments, the radiation source 12 and detector 28 are held fixed, and the object 24 is rotated.

The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and/or pre-patient collimator/filter assembly 22, and to process the digital measurements acquired by the detector 28 in accordance with the steps and processes discussed herein. In one embodiment, the system controller 30 may be implemented as all or part of a processor-based system.

The source 12 may be controlled by an X-ray controller 38 contained within the system controller 30. The X-ray controller 38 may be configured to provide power, timing signals, and/or focal spot size and spot locations to the source 12. In addition, in some embodiments the X-ray controller 38 may be configured to selectively activate the source 12 such that tubes or emitters at different locations within the system 10 may be operated in synchrony with one another or independent of one another or to switch the source 12 between different energy spectra (e.g., high- and low-energy spectra) during an imaging session.

The system controller 30 may include a data acquisition system (DAS) 40. The DAS 40 receives data collected by readout electronics of the detector 28, such as digital signals from the detector 28. The DAS 40 may then convert and/or pre-process the data for subsequent processing by a processor-based system, such as a computer 42. In certain implementations discussed herein, circuitry within the detector 28 may convert analog signals of the detector to digital signals prior to transmission to the data acquisition system 40. The computer 42 may include or communicate with one or more non-transitory memory devices 46 that can store data processed by the computer 42, data to be processed by the computer 42, or instructions to be executed by image processing circuitry 44 of the computer 42. For example, a processor of the computer 42 may execute one or more sets of instructions stored on the memory 46, which may be a memory of the computer 42, a memory of the processor, firmware, or a similar instantiation. By way of example, the image processing circuitry 44 of the computer 42 may be configured to generate a diagnostic image. In one embodiment, the diagnostic image is a real-time image obtained using image reconstruction techniques applied to the plurality of signals obtained from the plurality of pixels comprising detector 28. In one embodiment, the diagnostic image is a CT image displayed on a display device 50 for assisting a medical practitioner.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data (e.g., soft tissue images, bone images, segmented vascular trees, and so on), material basis images, and/or material decomposition results, and so forth. Additionally, the system 10 may include a printer 52 coupled to the operator workstation 48 and configured to print any desired measurement results. The display 50 and the printer 52 may also be connected to the computer 42 directly (as shown in FIG. 1) or via the operator workstation 48. Further, the operator workstation 48 may include or be coupled to a picture archiving and communications system (PACS) 54. PACS 54 may be coupled to a remote system or client 56, radiology department information system (RIS), hospital information system (HIS) or to an internal or external network, so that others at different locations can gain access to the image data.

Figure 2:
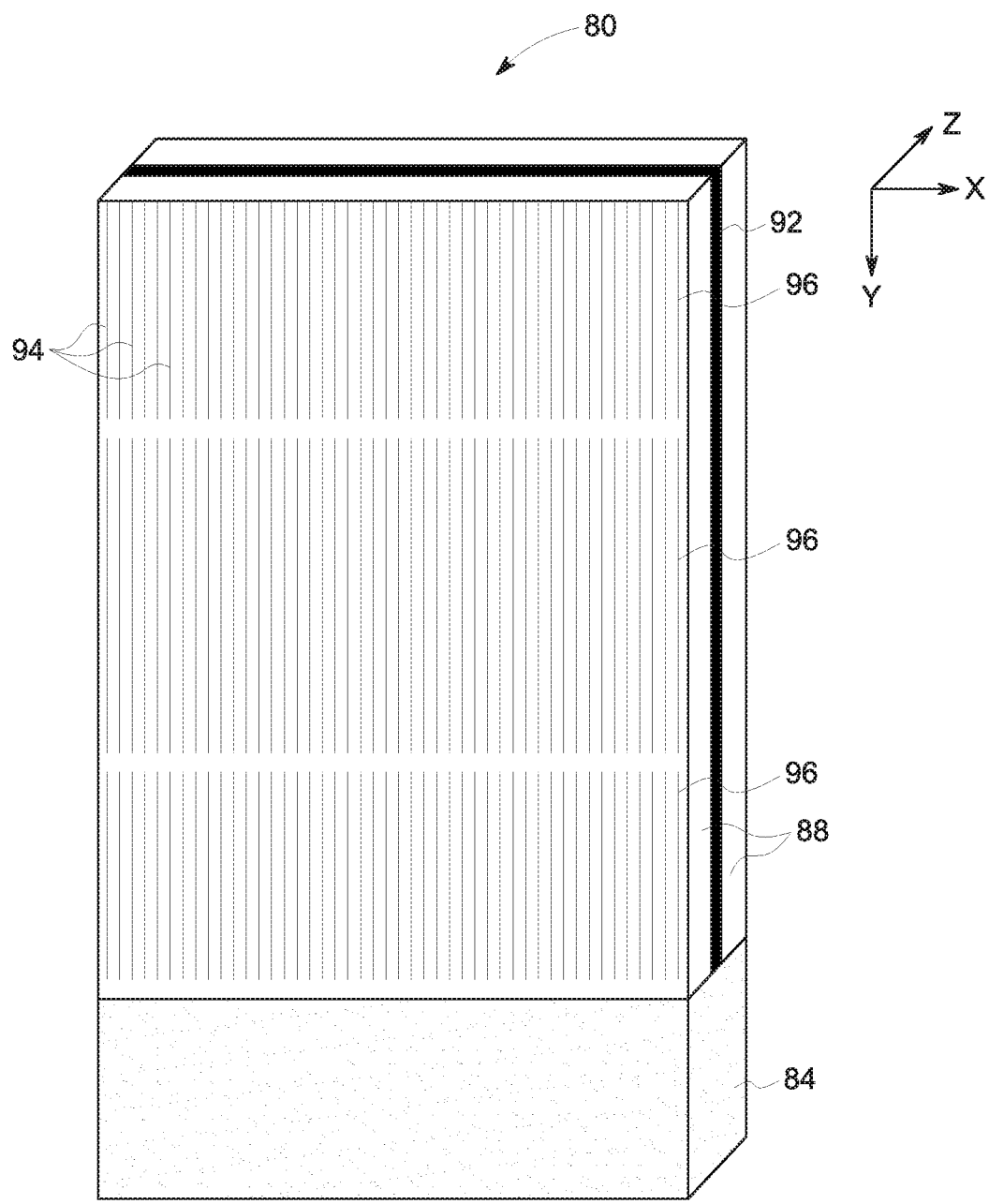
FIG. 2 depicts a perspective view of a section of a detector module comprising a sensor pair, in accordance with aspects of the present disclosure.

With the preceding discussion of an overall imaging system 10 in mind, and turning to FIG. 2, a portion of a detector module 80 for use in accordance with the present approach is shown in greater detail. In particular, in one embodiment the portion of detector module 80 may be a direct-conversion type detector module (i.e., the detector elements do not employ a scintillator intermediary), such as a detector based on semiconductor materials as the active material (e.g., silicon) that generates a measurable signal when the semiconductor sensor is itself exposed to X-ray photons. In the context of a pixelated detector 28 for use in CT, the detector 28 includes a plurality of such portions of detector module 80 arranged in two dimensions (e.g., the depicted X and Z dimensions) with respect to a cylindrical bore so as to cover the required imaging field of view for each angular position among the multiple angular positions at which X-rays are incident on the detector 28.

As used herein, the direction traveled by the X-rays 26 (i.e., the direction of X-ray propagation) with respect to the source-facing surface of the portion of detector module 80 may be denoted as "vertical" (corresponding to the Y dimension in FIG. 2) and/or may be construed as corresponding to a depth dimension so as to provide a geometric frame of reference. As will be appreciated, however, geometric characterizations such as "vertical" as used herein do not necessarily denote absolute position or orientation information, but are merely intended to simplify discussions by providing a consistent contextual framework. Furthermore, in alternate embodiments, the orientation of the detector with respect to the X and Z dimensions may be swapped. With this in mind, in certain implementations discussed herein a portion of detector module 80 includes vertically-segmented (i.e., segmented in the Y dimension) silicon substrates which may be addressed in discrete subunits corresponding to detector elements (i.e., pixels).

In one implementation, each portion of detector module 80 is fabricated from an assembly of sensor pairs. In the depicted example, and as shown in greater detail in the following figures, each sensor pair corresponds to readout electronics 84 attached to a pair of focally-aligned silicon wafers 88 extending in the Y dimension. Between each pair of wafers 88 within a given sensor pair, an X-ray attenuating material, e.g., a tungsten foil or divider, may be provided that acts as an internal collimator 92 within each respective sensor of the pair so as to reduce Compton scatter between detector elements. Multiple pairs of wafers 88 and internal collimator 92 may be combined to produce a detector module. The readout electronics 84 may comprise application specific integrated circuits (ASICs) that allow readout of signals from the wafers 88, connections or conductive traces to the wafers and to conductor terminals of the respective sensor pair, and so forth.

While the wafer thickness constrains the boundaries of the discrete detector elements in the Z dimension, the wafer represents a continuous substrate in the X dimension. In practice, each wafer 88 is patterned by electrodes using lithographic or other suitable techniques to define discrete detector elements on each wafer in the X dimension. Thus, each wafer 88 is patterned into separate detector elements (i.e., pixels) in the X dimension. This is schematically illustrated by the parallel lines 94 depicted on the foremost wafer 88 of FIG. 2.

Further, in the depicted example, each detector element may be vertically segmented (i.e., segmented in the Y dimension) such that each vertical segment 96 may be separately and/or independently read out, as denoted by the breaks in the lines 94. Such segmentation may be accomplished by electrode patterning on the wafer 88 and need not represent a physical or material break in the substrate. Each vertical segment, connected to a dedicated ASIC channel, is a fully-functional energy-discriminating photon-counting detector, producing detected counts in one or more energy bins. This topology allows measurement of different energy signals at each detector element location, both in the X-Z plane and also along the depth (y) direction. The energy-dependent information may be useful for material decomposition processing and other CT imaging techniques. Thus, in one such implementation, each detector element is effectively an elongated (i.e., high-aspect ratio) detector element that is vertically segmented. The segmentation reduces the likelihood of overlapping induced sensor signals arising from incident photons interacting with the sensor material (so called pile-up), thereby providing a detector configuration that has higher count rate performance before behaving non-linearly, i.e., recorded counts not linearly related to incident flux intensity.

Figure 3:
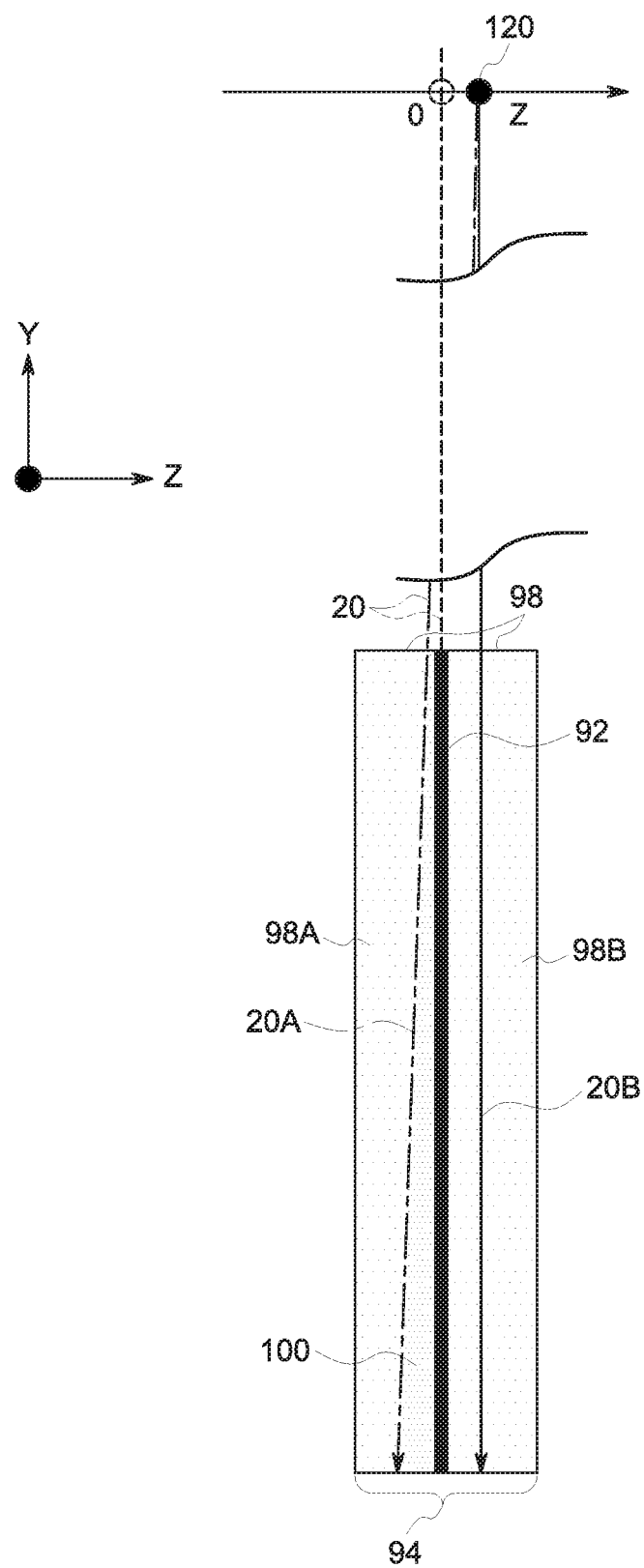
FIG. 3 depicts a schematic side view of detector elements of a sensor pair with respect to an X-ray focal spot position, in accordance with aspects of the present disclosure.

Turning to FIG. 3, certain of the above described structures and their spatial arrangement may be more readily conceptualized from a schematic, sectional view presented in this figure. In this sectional schematic view, a sensor pair 94 is depicted that encompasses a pair of detector elements 98 (defined by electrode patterning and the boundary of the wafer substrate), here left detector element 98A and right detector element 98B, separated by a tungsten collimator 92 within the sensor pair 94. In one implementation, the thickness of wafer 88 is approximately 600 μm and the thickness of tungsten collimator 92 is approximately 50 μm.

In the depicted example, an X-ray emission focal spot 120 is also depicted along the Z-dimension axis. The focal spot 120 may move along the Z-dimension axis during CT operation as a result of heating of the anode or due to gantry rotation. As may be appreciated, due to the geometry of the collimation and the pairing of the detector elements 98 (e.g., left detector element 98A and right detector element 98B) within each sensor pair 94, there may be a detector element for which X-rays 20 are more or less attenuated by collimator 92. For example, a detector element on which the incident X-ray are less attenuated by the respective collimator 92 (here right detector element 98B, as illustrated by unimpaired passage of X-ray 20B) and a detector element on which the incident X-rays are more attenuated by the collimator 92 (here left detector element 98A, as illustrated by X-ray 20A being limited by the collimator 92, casting shadow 100) are shown. As the scan is performed and/or as the focal spot 120 moves along the Z dimension, which detector element is better illuminated by X-rays and which is less illuminated within a given sensor pair 94 may change. As may be appreciated, however, the incidence of X-rays on a given pair of detector elements 98A, 98B within a sensor pair 94 is complementary, i.e., symmetric about a perfectly aligned position, due to their geometric relationships such that as the X-ray incidence on one decreases due to shadowing by the collimator 92, the incidence on the other increases as it emerges from the shadow. In alternate embodiments, the signals or measurements from detector elements 98 comprise signals from one or more individual detector segments, or combinations of the signals from one or more detector segments, wherein combination refers to direct summing or weighted summing of the signals from individual detector segments.

Based on these considerations, it may be appreciated that the gain g of a given detector element 98 (i.e., pixel) is impacted by the position of the focal spot 120 in the Z dimension. With this in mind, a transfer function may be derived based on the measured signal acquired by a detector element 98 as a function of focal spot position in the Z dimension. An example of one such transfer function is:

$$g(z) = \left(\frac{G(z)}{G(0)} - 1\right) \quad (1)$$

where g(z) is the gain of a respective detector element when the focal spot 120 is at position z, and where G(z) and G(0) respectively are measured signal counts from a pixel segment when the focal spot is at position z and position 0, respectively. This transfer function, or other suitable functions specific to a given scanner, scanner model, detector, or detector model, may be generated based on empirical measurement by measuring the signal generated by paired detector elements within a respective sensor pair 94 at different focal spot positions along the Z dimension. Because, as noted above, these paired detector elements 98 are complementary in terms of their measurements, their respective transfer functions are also complementary.

Figure 4:
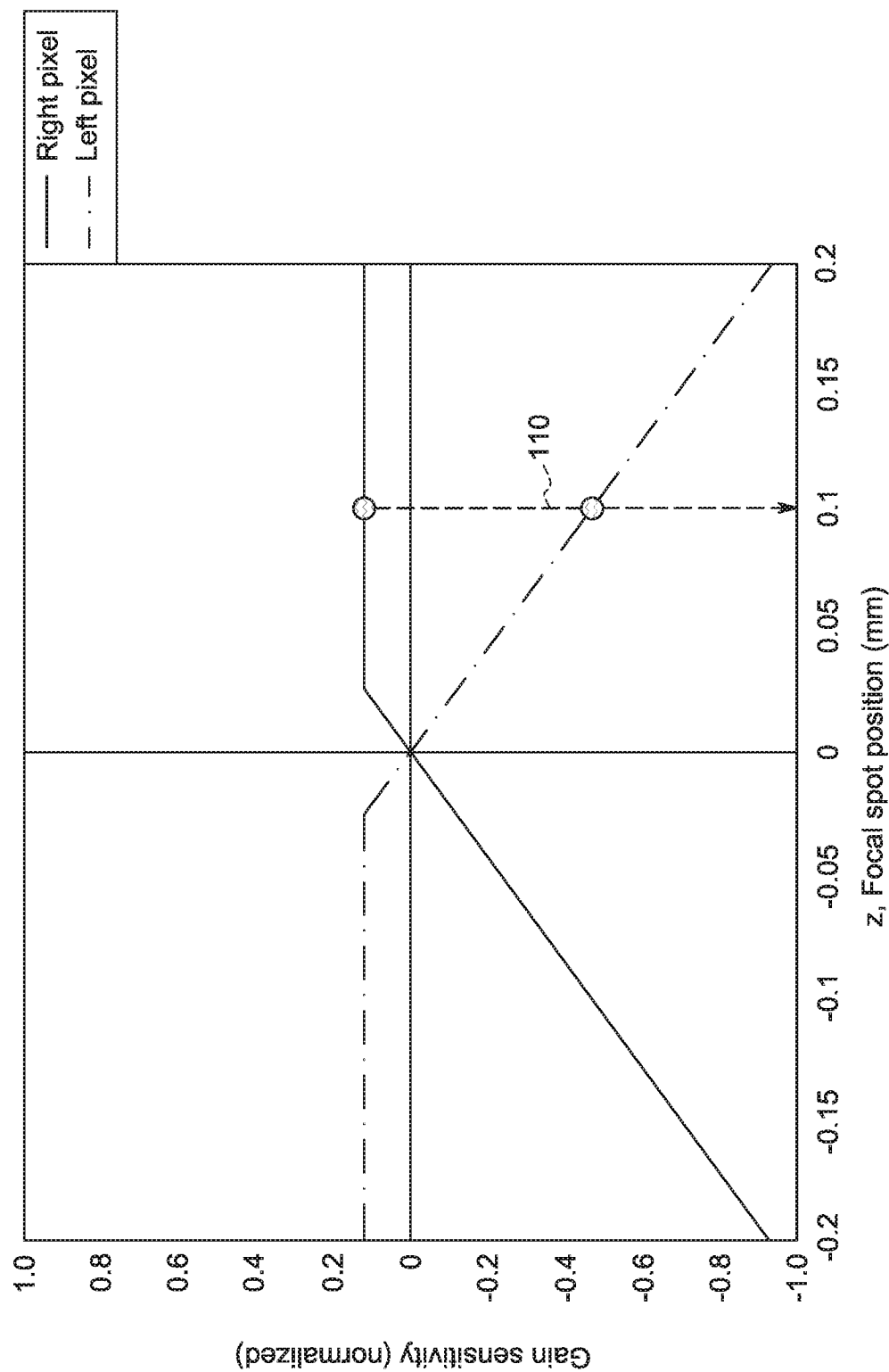
FIG. 4 depicts a graphical representation of complementary response functions for a sensor pair, in accordance with aspects of the present disclosure.

The variable gain as a function of z position is illustrated by a graphical plot in FIG. 4 of one example of right detector element 98B, and left detector element 98A gain response at different focal spot positions in z, with z=0 representing the focal spot position in alignment with the paired detector elements. As shown, the respective gain functions for the paired detector elements are symmetric or complementary. As may be further appreciated, based on these determinable empirical relationships for a pair of detector elements 98, a given set of measurements acquired using the respective detector elements 98 of a sensor pair 94 may be evaluated or compared to a graph (such as that depicted) or a corresponding look-up table to determine the focal spot position in the Z dimension for that measurement. By way of example, FIG. 4 depicts a pair of measurements for both a right and left detector element and the corresponding focal spot position in z, as denoted by dashed line 110. Although not shown in FIG. 3, the methodology will accommodate a finite focal spot size. Moreover, although the methodology is discussed with reference to focal spot motion in the Z dimension, the approach is not limited to this dimension and may be used to appropriately accommodate motion where sensor pairs 94 are suitably oriented.

Figure 5:
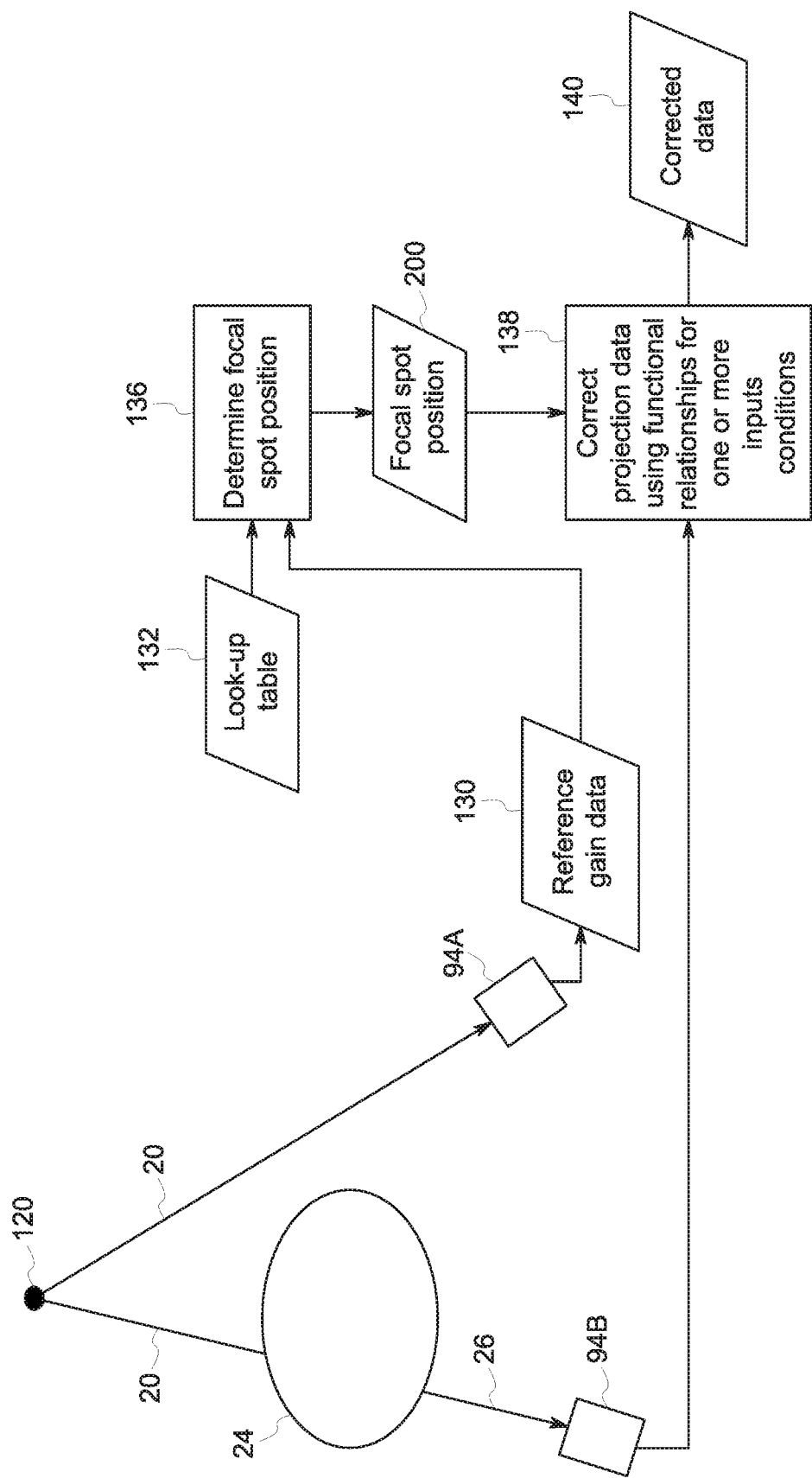
FIG. 5 illustrates a correction procedure using an estimated focal spot position, in accordance with aspects of the present disclosure.

With the preceding in mind, in certain implementations, the ability to obtain an estimate or measure of focal spot position in the Z dimension during a scan may be leveraged in various ways. For example, turning to FIG. 5, an example is depicted in which sensor pairs on a portion(s) of a detector exposed to unattenuated X-ray emissions 20 (i.e., sensor pairs positioned outside the field-of-view (FOV), depicted as reference sensor pair(s) 94A) are used to estimate focal spot Z position 120. Data acquired by sensors pairs 94 of the detector exposed to X-rays 26 attenuated by the patient 24 or object undergoing imaging (depicted as active sensor pair(s) 94B) may then be adjusted or corrected to account for the estimated focal spot Z position 120 (i.e., focal spot misalignment).

In this example, reference gain data 130 acquired via the reference sensor pair(s) 94A during an examination may be compared to a look-up table 132 or graph, such as discussed with respect to FIG. 4, such that the reference gain data 130 at a given point in time provides an estimate (i.e., determination step 136) of the position of the focal spot 120 in the Z dimension at that time. The determined focal spot position 200 may then be used to correct (step 138) projection data acquired by the active sensor pair(s) 94B at that time, as discussed in greater detail below, to generate corrected projection data 140 which may then be processed (e.g., reconstructed) as normal.

By way of example, in a multi-energy context where different energy bin data is collected at different vertical segments of the detector elements 98, calibration data may be initially generated for different combinations (i.e., different percentages) of water, bone, and contrast at the different vertical segments of the detector elements 98 for different Z positions of the focal spot. In this manner, when focal spot Z positions are determined, the appropriate calibration corrections may be applied to the projection data acquired by the active sensor pairs.

Figure 6:
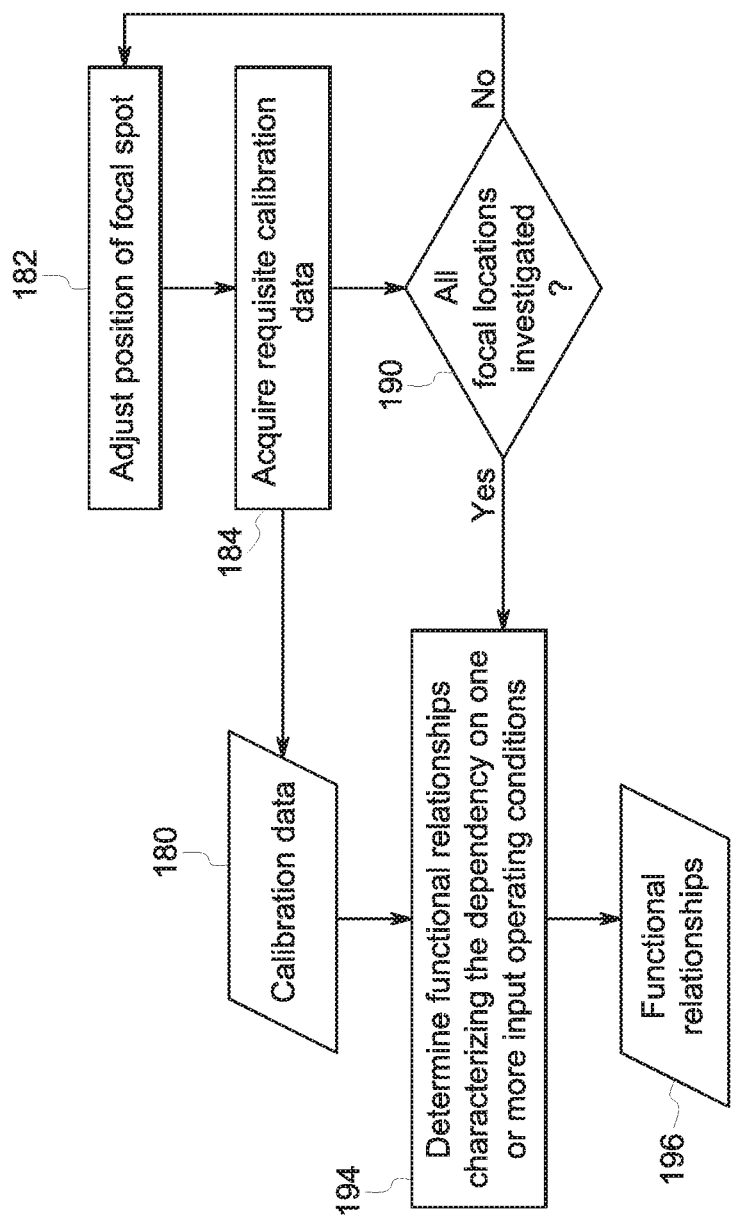
FIG. 6 illustrates a process for generating calibration data, in accordance with aspects of the present disclosure.

An example of a process for generating such calibration data 180 is shown in FIG. 6. In this example, the position of the focal spot 120 may be adjusted (step 182) by electromagnetically steering the electron beam impinging on the anode of an X-ray tube in either the axial or transaxial directions. For a given position of the focal spot 120, calibration data 180 is acquired (step 184) and the focal spot 120 moved to the next position in Z (or X) until all positions of interest have associated calibration data 180 (as determined at decision block 190). As used herein, calibration data 180 may include CT projection data acquired for various defined or determinable operating conditions associated with the calibration scan (e.g., operating voltage of the operating tube, levels of pile-up in the detector, mA setting of the X-ray tube, the combination of materials in the X-ray beam path for spectral calibration, and so forth). The number of focal spot positions sampled for a calibration process may be based on the functional dependency of the correction(s) on the specific operating conditions noted above and the number of operating conditions to be characterized. Once calibration data 180 is acquired for all focal spot positions of interest, functional relationships 196 may be determined (step 194) using the calibration data 180 that characterize the dependency of the calibration measurements on one or more of the input operating conditions. In practice, these functional relationships 196 may be characterized by response surfaces, look-up tables, and so forth.

Figure 7:
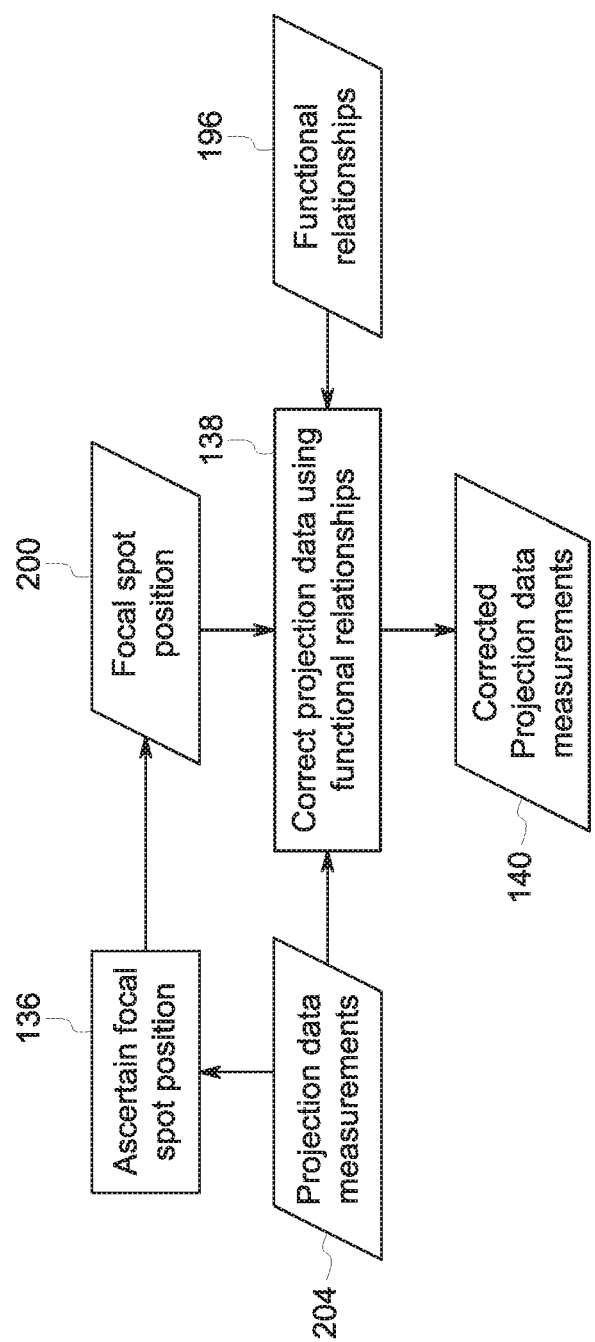
FIG. 7 illustrates additional aspects of a correction procedure using an estimated focal spot position, in accordance with aspects of the present disclosure.

As will be appreciated, and turning back to FIG. 5, these functional relationships 196, the known operating conditions for a given scan, and the determined position of the focal spot 120, may be used at step 138 to correct projection data acquired by the active sensor pairs 94 that acquire data characterizing X-ray transmission through the patient 24. This may be done in a real-time or concurrent manner, or post hoc. A process flow for such a correction process for correcting measurement data is shown in FIG. 7. In this example, building on the concepts described above, the position 200 of the focal spot 120 is determined (step 136) as described above with respect to FIG. 5, such as using projection data measurements 204 acquired by a reference sensor pair(s) 94A. Based on the focal spot position 200 and functional relationships 196 with operating conditions derived during prior calibration, projection data measurements 204 acquired using active sensor pair(s) 94B may be corrected (step 138) to generate corrected projection data measurements 140. Note that the collection of projection data measurements 204 can be used to estimate one or more focal spot positions 200 during scanning procedures. For example, projection data measurements 204 collectively can be used to estimate an average focal spot position 200 during scanning, or each projection data measurement, corresponding to a particular orientation of the X-ray source and detector to the object being scanned, can be used to estimate the focal spot position 200 on a view-by-view basis.

While measurement data correction is one possible implementation, it may be appreciated that, in other embodiments, real-time knowledge of the position focal spot 120 in the Z dimension may be used to adjust the focal spot position in real-time so as to maintain its alignment with the detector elements. For example, in one such embodiment the position of the focal spot 120 in the Z dimension may, as determined from measurements by reference sensor pair(s) 94A, may be provided as an input to the X-ray controller 38, which may adjust the focal spot position to account for drift away from the intended focal spot position. In particular, once the position of the focal spot 120 is known, it may be adjusted by electromagnetically steering the electron beam impinging upon the anode in the X-ray tube so as to compensate for any drift in the position of the focal spot 120. In this manner, correction of the projection data for focal spot drift can be avoided as the focal spot is instead maintained in alignment throughout acquisition of projection data for image reconstruction.

As discussed herein, technical effects of the invention include reduction of focal spot motion induced artifacts in CT images. In particular, the techniques for adjusting focal spot motion during scanning allow for real-time estimation of the misalignment of an X-ray focal spot and X-ray detectors using high aspect ratio detector elements. Technical and commercial advantages include, but are not limited to: (1) maintaining image quality in single-energy and multi-energy images at all, i.e., low-dose to high-dose, imaging protocols using electrostatic and electromagnetic steering of the electron beam in real-time; (2) reduced time required for calibration procedures and complexity of same-both for installation calibration and daily calibration procedures executed at the customer site.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for generating calibration data, comprising:
   emitting X-rays from a focal spot of an X-ray source at a plurality of focal spot positions in one or more spatial dimensions;
   for each position, generating paired response data, wherein the paired response data comprises a first measurement from a first detector element of a sensor pair and a second measurement from a second detector element of the sensor pair, wherein the first detector element and the second detector element of the sensor pair have complementary response functions with respect to movement of the focal spot in the one or more dimensions, wherein the first detector element and the second detector element of the sensor pair are disposed adjacent to each other, and wherein the complementary response functions are symmetric about a perfectly aligned focal spot position so that the X-rays incident on one of the first detector element or the second detector element decreases as the X-rays incident on the other of the first detector element or the second detector element increases; and
   associating at least the paired response data and corresponding positions in the one or more spatial dimensions to generate one or more functional relationships.

2. The method of claim 1, wherein the one or more spatial dimensions include a spatial dimension in a slice direction along a bore of a computed tomography (CT) scanner.

3. The method of claim 1, wherein the sensor pair comprises an attenuating layer positioned between the first detector element and the second detector element, wherein X-ray attenuation caused by the attenuating layer causes the complementary response functions of the first detector element and the second detector element with respect to position of the focal spot in the one or more spatial dimensions.

4. The method of claim 3, wherein the first detector element and the second detector element of the sensor pair comprise a low atomic number conversion material having a sufficient thickness in a spatial dimension corresponding to the direction of X-ray travel to discern a complementary response function.

5. The method of claim 1, wherein the one or more functional relationships further incorporate one or more operating conditions in addition to the paired response data and the corresponding positions in the one or more spatial dimensions.

6. The method of claim 5, wherein the one or more operating conditions comprise an operating voltage of the X-ray tube, a level of pile-up in the detector, an mA setting of the X-ray tube, or a combination of materials in the X-ray beam path for spectral calibration.

7. The method of claim 1, wherein the one or more functional relationships comprise one or more of response surfaces or look-up tables.

8. A method of addressing X-ray focal spot misalignment, comprising:
  emitting X-rays from an X-ray source comprising a focal spot, wherein the X-rays pass through an imaging volume in which a patient or object being scanned is positioned;
  acquiring response data from one or more reference sensor pairs positioned where the X-rays incident on the reference sensor pairs do not pass through the patient or object, wherein the response data for each reference sensor pair comprises a first measurement from a first detector element of the respective sensor pair and a second measurement from a second detector element of the respective sensor or pair, wherein the first detector element and the second detector element of the each reference sensor pair have complementary response functions with respect to movement of the focal spot in one or more spatial dimensions, wherein the first detector element and the second detector element of each reference sensor pair are disposed adjacent to each other, and wherein the complementary response functions are symmetric about a perfectly aligned focal spot position so that the X-rays incident on one of the first detector element or the second detector element decreases as the X-rays incident on the other of the first detector element or the second detector element increases;
  determining a position in the one or more spatial dimensions of the focal spot using the response data from the one or more reference sensor pairs; and
  performing corrective action based on the position of the focal spot in the one or more spatial dimensions.

9. The method of claim 8, wherein the one or more spatial dimensions include a spatial dimension in a slice direction along a bore of a computed tomography (CT) scanner.

10. The method of claim 8, wherein the one or more reference sensor pairs each comprise an attenuating layer positioned between the first detector element and the second detector element of the respective reference sensor pair, wherein X-ray attenuation caused by the attenuating layer causes the complementary response between the first detector element and the second detector element with respect to position of the focal spot in one or more spatial dimensions.

11. The method of claim 8, further comprising acquiring additional response data from a plurality of active sensor pairs positioned where the incident X-rays on the active sensor pairs pass through the patient or object.

12. The method of claim 11, wherein performing corrective action comprises:
  based on the position in the one or more spatial dimensions of the focal spot, determining one or more corrective actions to perform on the additional response data based on one or more previously determined functional relationships, wherein the functional relationships are derived for different positions of the focal spot in the one or more spatial dimensions and one or more different operating conditions.

13. The method of claim 12, wherein the one or more functional relationships comprise one or more of response surfaces or look-up tables.

14. The method of claim 12, wherein the different operating conditions comprise one or more of an operating voltage of the X-ray tube, a level of pile-up in the detector, an mA setting of the X-ray tube, or a combination of materials in the X-ray beam path for spectral calibration.

15. The method of claim 8, wherein performing corrective action comprises adjusting the position of the focal spot to correct for deviation of the position of the focal spot.

16. An X-ray imaging system, comprising:
  an X-ray source configured to emit X-rays from a focal spot during operation;
  a detector configured to generate signals corresponding to X-ray intensity when exposed to X-ray emission by the X-ray source, wherein the detector comprises a plurality of sensor pairs, each sensor pair comprising a first detector element and a second detector element separated by an attenuating layer and having complementary response functions with respect to position of the focal spot in one or more spatial dimensions, wherein the first detector element and the second detector element of each sensor pair are disposed adjacent to each other, and wherein the complementary response functions are symmetric about a perfectly aligned focal spot position so that the X-rays incident on one of the first detector element or the second detector element decreases as the X-rays incident on the other of the first detector element or the second detector element increases;
  one or more processing circuits configured to:
    cause emission of X-rays from the X-ray source, wherein the X-rays pass through an imaging volume in which a patient or object being scanned is positioned during operation;
    acquire response data from one or more reference sensor pairs of the plurality of sensor pairs, wherein the reference sensor pairs are positioned where the X-rays incident on the reference sensor pairs do not pass through the patient or object;
    determine a position of the focal spot in the one or more spatial dimensions using the response data from the one or more reference sensor pairs; and
    perform corrective action based on the position of the focal spot in the one or more spatial dimensions.

17. The X-ray imaging system of claim 16, wherein the X-ray imaging system comprises a computed tomography (CT) imaging system.

18. The X-ray imaging system of claim 16, wherein the one or more spatial dimensions include a dimension in a slice direction of the X-ray imaging system.

19. The X-ray imaging system of claim 16, wherein the first detector element and the second detector element of the sensor pairs comprise a low atomic number conversion material having a sufficient thickness in a spatial dimension corresponding to the direction of X-ray travel to discern a complementary response function.

20. The X-ray imaging system of claim 16, wherein the one or more processing circuits are further configured to acquire response data from one or more active sensor pairs of the plurality of sensor pairs, wherein the active sensor pairs are positioned where the X-rays incident on the active sensor pairs pass through the patient or object.

21. The X-ray imaging system of claim 20, wherein the one or more processing circuits are further configured to perform corrective action by determining one or more corrective actions to perform on the response data acquired by the active sensor pairs based on one or more previously determined functional relationships, wherein the functional relationships are derived for positions of the focal spot in the one or more spatial dimensions and one or more different operating conditions.

22. The X-ray imaging system of claim 16, wherein the one or more processing circuits are further configured to perform corrective action by adjusting the position of the focal spot to correct for deviation of the position of the focal spot.

* * * * *